United States Patent
Legen et al.

(10) Patent No.: US 8,642,078 B2
(45) Date of Patent: Feb. 4, 2014

(54) COATED FORMULATIONS FOR TOLTERODINE

(75) Inventors: Igor Legen, Grosuplje (SI); Polonca Kuhar, Ljubljana (SI)

(73) Assignee: Lek Pharmaceuticals, D.D., Ljubljana (SI)

( * ) Notice: Subject to any disclaimer, the term of this patent is extended or adjusted under 35 U.S.C. 154(b) by 831 days.

(21) Appl. No.: 12/294,571

(22) PCT Filed: Mar. 29, 2007

(86) PCT No.: PCT/EP2007/053027
§ 371 (c)(1),
(2), (4) Date: Dec. 17, 2008

(87) PCT Pub. No.: WO2007/113207
PCT Pub. Date: Oct. 11, 2007

(65) Prior Publication Data
US 2009/0214642 A1    Aug. 27, 2009

(30) Foreign Application Priority Data
Mar. 31, 2006    (EP) ..................... 06006979

(51) Int. Cl.
*A61K 9/54*    (2006.01)
*A61K 9/62*    (2006.01)
*A61K 9/20*    (2006.01)
*A61K 31/205*    (2006.01)

(52) U.S. Cl.
USPC ........... 424/458; 424/457; 424/461; 424/464; 514/648; 514/653

(58) Field of Classification Search
None
See application file for complete search history.

(56) References Cited

U.S. PATENT DOCUMENTS

| 4,138,475 | A | 2/1979 | McAinsh et al. |
| 5,188,841 | A | 2/1993 | Simpkin et al. |
| 5,273,760 | A * | 12/1993 | Oshlack et al. ............... 424/480 |
| 6,911,217 | B1 | 6/2005 | Gren et al. |
| 2004/0191345 | A1 * | 9/2004 | Nicklasson et al. .......... 424/776 |

FOREIGN PATENT DOCUMENTS

| EP | 1 629 834 A1 | 3/2006 |
| EP | 1 810 668 A1 | 7/2007 |
| WO | WO 2004/066974 A1 | 8/2004 |
| WO | WO 2004/105735 A1 | 12/2004 |
| WO | WO 2006/021425 A1 | 3/2006 |

OTHER PUBLICATIONS

Pollock et al.The Utility of HydroxypropylMethylcellulose as a Porosity Modifier in an Ethylcellulose Compression Coating. Presented at the 27th International Symposium on Controlled Release of Bioactive Materials, Paris, France, Jul. 7-13, 2000.*
[Disclosed Anonymously]; Sustained release pharmaceutical composition of tolterodine; IP.com Journal; Jul. 26, 2006; West Henrietta, NY, 20006; ISSN 1533-0001.

* cited by examiner

*Primary Examiner* — Lakshmi Channavajjala
(74) *Attorney, Agent, or Firm* — Arent Fox LLP

(57) ABSTRACT

A sustained release pharmaceutical composition comprising coating comprising at least one water-insoluble permeable polymer and at least one water soluble polymer and homogenous cores containing only tolterodine or a salt thereof and microcrystalline cellulose is described.

11 Claims, 1 Drawing Sheet

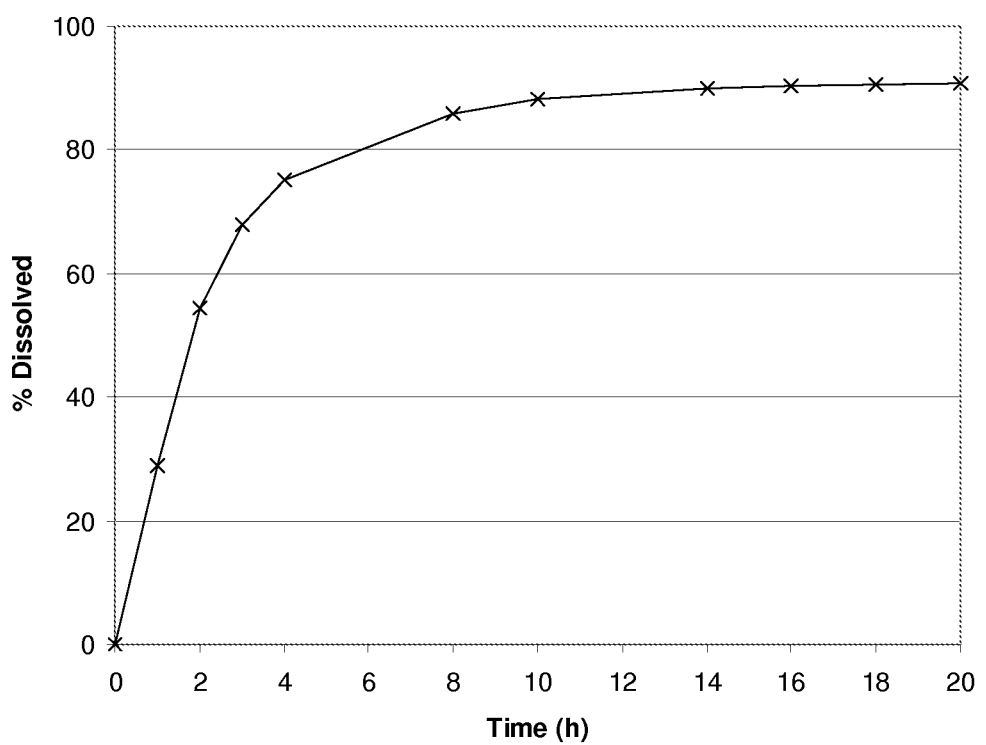

COATED FORMULATIONS FOR TOLTERODINE

CROSS-REFERENCE TO RELATED APPLICATION

This application is a National Stage entry of International Application No. PCT/EP2007/053027, filed Mar. 29, 2007, which claims priority to European Patent Application No. 06006979.6 filed Mar. 31, 2006, the entire specification claims and drawings of which are incorporated herein by reference.

FIELD OF THE INVENTION

The present invention relates to the field of pharmaceutics, and specifically to pharmaceutical formulations of tolterodine, or its salts, specifically tartrate salt; more specifically to sustained release formulations of tolterodine comprising multiple individual units and preferably to pellets filled into capsules.

BACKGROUND OF THE INVENTION

Compositions providing for sustained release of an active pharmaceutical ingredient (active) are generally made by applying various layers containing said active over inert core, whereas the penetration of gastric or intestinal fluid through those layers dictates the kinetics of release or alternatively by incorporating the active into a core, for example into a tablet whereas the kinetics of release is dictated by slow disintegration/dissolution of said tablet.

Such core must according to EP 1629834 A1 contain a combination of more than one excipients. It is postulated that pellets prepared only with microcrystalline cellulose and tolterodine are insufficiently strong and also provide an insufficiently controlled release of the active substance tolterodine The present invention is aimed at preparation of a simple immediate release pharmaceutical composition (e.g. tablets), which can be administered more than once a day, but also a preparation of a sustained release composition, by applying to said immediate release composition preferably only one coating layer which provides for sustained release.

If desired, an additional layer may be applied as anti-tacking, protective or cosmetic coat, e.g. if the composition is to be uses in sprinkle capsules, to be sprayed onto food, an additional taste masking layer may be advantageous.

DISCLOSURE OF THE INVENTION

Our invention provides for a sustained release pharmaceutical composition comprising: a coat comprising at least one water-insoluble permeable polymer and at least one water soluble polymer applied onto homogenous cores containing only tolterodine and microcrystalline cellulose; which may be filled into capsules or alternatively compressed in tablets. The cores are preferably pellets made by extrusion and spheronization and may optionally further comprises an additional coat. The amount of tolterodine in cores is from 0.5 to 10% wt, in particular around 2 to 3%. Tolterodine encompasses salts thereof, in particular tartrate.

The characteristic of the manufacturing process is that the pellets which are made by extrusion spheronisation are homogenous. Alternatively the cores are homogenous granules, prepared by any suitable method. The alternative methods of preparation of cores are wet granulation or powder compaction or similar. In all the above methods the exact predetermined weight of active and microcrystalline cellulose are mixed, thus allowing good control of amount of active from the start as compared to alternative methods where the active is applied to cores in less controllable process of sugar or film coating of inert cores and the amount may be determined by in-process analytics.

Aspect of the invention represents the ratio of water-insoluble permeable and the water soluble polymer, which is from 5 to 20, in particular 8 to 18, more particularly around 8 to 13, and 8 to 10 and the water soluble polymer is hydroxypropylmethyl cellulose, more particularly having a viscosity from 10 to 100 cP, particularly 10 to 30 cP, preferably 12 to 18 cP and preferably the water-insoluble permeable polymer is ethylcellulose in particular when used in dispersion where ethylcellulose comprises small amount of oleic acid, such as sold under tradename Surelease.

Our invention is embodied in a process for the manufacture of a sustained release pharmaceutical composition consisting of steps:

preparing homogenous cores containing only tolterodine and microcrystalline cellulose, in particular preparing pellets by extrusion and spheronization; and coating said cores (in particular pellets) with a coat comprising at least one water-insoluble permeable polymer and at least one water soluble polymer.

The weight of coating in accordance with our invention represent from 5 to 20%, in particular 7 to 15%, more in particular 9 to 12% to the weight of coated cores. Such coat predominantly controls the sustained release of an active from pharmaceutical composition providing desired release profile. However with HPMC viscosity around 15 cP, the variability of amount of coating (between 9 and 12%, by weight to core) has little effect on the desired release profile.

The aspect of the invention is also the use of pellets containing only tolterodine and microcrystalline cellulose for manufacturing of a pharmaceutical composition. Such pellets without a coat may be used to prepare an immediate release pharmaceutical composition, or once coated in accordance with our invention can be used in subsequent steps where one or more coats providing for modified release and/or taste masking and/or stability enhancement is applied.

The aspect of the invention is also a coating for pharmaceutical composition comprising ethylcellulose and hydroxypropylmethylcellulose with viscosity in range 12 to 18 cP, where weight ratios of ethylcellulose and hydroxypropylmethylcellulose are between 8:1 and 13:1, (preferably 8-10:1) and where the weight of said coating is between 9 and 12% by weight relative to weight of coated composition.

DETAILED DESCRIPTION OF THE INVENTION

In accordance with our invention we have developed a pharmaceutical composition wherein desired controlled release profile is enabled with, preferably multiple units, pharmaceutical formulation comprising cores coated with single layer. The cores may be filled into capsules or compressed into tablets, wherein cores may be granules, tablets, but preferably pellets; and a coating comprises a combination of release modifying polymers, such as hydrophilic (water soluble) and water-insoluble bur permeable polymers.

In the preferred embodiment the pellets, which are spherical or spheroidal shape and contain substantially homogenously distributed constituents, and are substantially uniform in size are made by extrusion and spheronisation. Surprisingly pellets consisting only of tolterodine and microcrystalline cellulose prepared by this process are sufficiently strong and when coated with above coating provide sufficiently controlled release. The pellets consisting only of tolterodine tartrate and microcrystalline cellulose prepared by extrusion and spheronisation are strong and when coated with above coating provide desired release profile.

The desired release profile means that an active pharmaceutical ingredient is released in a constant manner, preferably extended as compared to immediate release formulation, what can be assessed by measuring the dissolved amount of the active pharmaceutical ingredient by the dissolution test in vitro or when administered orally in vivo by following the pharmacokinetic parameters i.e. Cmax, tmax of tolterodine and its metabolite.

Sustained release, as measured in vitro, means that 15-55% of tolterodine will be detected in solution after 2 hours, 30 to 80% (in particular 30-70%) in 3 hours, 40 to 90% (in particular 40-80%) in 4 hours, 60 to 99% in 8 hours and more than 85% in 16 hours, when subjected to dissolution test according to USP, using Apparatus 1 (rotating basket) at 100 rpm with 900 ml of phosphate buffer (50 mM) at pH 6.8 and 37° C. (all the measurement in this applications are made under this conditions); or alternatively means that measuring in vivo the maximum serum concentration of tolterodine or its 5-hydroxymethyl metabolite (Cmax) will be obtained substantially later (tmax) than with an immediate release formulation wherein Cmax is obtained approximately 0.5-1.5 hours (tmax) after oral administration, preferably the mean maximum serum concentration will be obtained in 3-13 hours; or that mean maximum obtained serum concentration obtained will be substantially lower than at the equal daily dose of an immediate release formulation, which is for daily dose of 4 mg approximately 5 ng/ml, preferably the mean maximum serum concentration will be less than approximately 4 ng/ml, for a dose of 4 mg. The sustained release formulation in accordance with our invention will thus after oral administration provide a substantially constant serum level of active moiety, defined as the sum of the concentration of unbound tolterodine and the concentration of unbound 5-hydroxymethyl metabolite of tolterodine, for 24 hours, which means ratio of maximum and minimum serum concentration (Cmax/Cmin) will be bellow 4.

Such composition can be easily prepared by short, simple and cost effective production process. The active substance is incorporated into homogenous cores, preferably pellets which in addition to the active substance contain only an inert diluent, preferably a cellulose, more preferably microcrystalline cellulose.

Cores may be prepared by conventional techniques, such as direct rotor pelletization, thermoplastic pelletization, solution and suspension layering, dry powder layering, spray dry agglomeration, whereas pellets are preferably prepared by extrusion and spheronisation of granulated powder mixture. The diameter of cores is usually from about 0.5 to 2.00 mm, preferably from about 0.5-1.2 mm.

Such cores are suitable for manufacturing a medicament, providing immediate release, by (for example) filling them into capsules or compressing thus prepared cores into tablets. There is a manufacturing advantage of being able to use those cores in further steps also for manufacturing a sustained release medicament. To achieve this, in the next step, a controlled release coating is applied to the cores. The weight of coating will represent from 5 to 20%, preferably 10-15%, most preferably around 9-12% to the weight of coated cores. In the coating also a lubricant such as talc may be used.

Such coating comprises two types of polymers: one or more water-insoluble permeable polymers and one or more water-soluble (hydrophilic) polymers in ratio between 5 to 1 and 20 to 1, preferably 6-18 to 1, most preferably around 8-10 to 1. It is preferred to use such combination of polymers, because applying only water-insoluble permeable polymer into an uniform coat is technologically more demanding if a thin coat is desired and deviations could result in rapid drug release at low coatings loads and very slow, incomplete drug release at high coating loads. On the other hand if the amount of water-soluble polymer is higher than 25% by weight of the coating, the rapid onset of release may result, which can be partially compensated by coating thickness.

Water-soluble (hydrophilic) polymer will have a characteristics of being substantially soluble in water, For example at least 100 mg of such polymer (e.g. HPMC E15LV) is soluble in 1 ml of demineralised water at 20° C., while may form a gel at higher temperature (e.g. at 56° C. 2% aqueous solution "E" type of HPMC is a gel). Preferable water-soluble (hydrophilic) polymers are hydroxypropylmethylcellulose (HPMC), hydroxypropylcellulose (HPC), more preferable HPMC having viscosity below 1000 cP, more preferably between 10 cP and 100 cP.

Water-insoluble permeable polymers are those that are not soluble in water or digestive fluid at temperatures between 15 and 25° C., meaning that in order to dissolve such polymer, more than 1 L, preferably 10 L of solvent is used per gram of solute. Such polymers may be acrylates, such as acrylate and/or methacrylate polymers and copolymers. such polymers may be Eudragit NE, or combination of Eudragit RS and Eudragit, polyvinyl acetate. Preferably such polymers will be ethylcellulose or polymethacrylate esters, however most preferably ethylcellulose. In pellets consisting only of microcrystalline cellulose and tolterodine and a coating comprising above mentioned Eudragit, the amount of degradation product, when subjecting so prepared and coated pellets to stability studies, increases compared to pellets coated with ethylcellulose.

The coating will in contact with aqueous environment swell and/or erode and therefore increase the permeability from the core for dissolved active ingredient. The release will be governed by coat thickness and above ratio of polymers.

The weight ratio of water-insoluble permeable and water soluble polymers in the coating will depend on the desired prolongation of Tmax, and will preferably be above 5:1. If any other excipients is used in coating this means that the weight amount of water soluble polymer will be less than 20% weight relative to the coating, more preferably 5 to 15%, most preferably when water soluble polymer with viscosity between 12 and 18 cP is used, (such as HPMC E15LV), around 8-13%. In this specific viscosity range either variation of ratio of water-insoluble permeable and water soluble polymer in range 8-10:1, or variation of the amount of coating relative to the weight of coated cores in range 9-12% wt has little effect on the desired release profile.

In this specific embodiment the desired release profile will be represented by a composition from which from 10% to 40% of tolterodine will be detected in solution in 1 hour; 50% to 75% in 3 hours, 70% to 90% in 4 hours, 80% to 99% in 8 hours, when subjected to dissolution test according to USP, using Apparatus 1 (rotating basket) at 100 rpm with 900 ml of phosphate buffer (50 mM) at pH 6.8 and 37° C. Thus the manufacturing process according to our invention is surprisingly robust as the desired release profile is achieved by coatings comprising ethylcellulose and HPMC at unexpectedly high variations on coating thickness, and allowing some variance in ratios of both polymers.

The coating is applied by any conventional coating method, preferably by spraying the polymer dispersion, which may in addition to two types of polymers described above comprise any other additional commonly used coating excipient, such as talc, in fluid-bed devices such as e.g. Glatt GPCG with Wurster insert, Huettlin Kugelcoater and the like.

The composition may be filled into capsules, compressed into tablets, or filled into sachets. If desired the composition may comprise additional coating, which does not influence the release of tolterodin from the composition. Such coating dissolves or disintegrates immediately, preferably in 10 minutes or less, after ingestion or after submitting such coating composition to a dissolution to at least 20 fold volume of water at room temperature. Such coating may contain excipients providing for pleasant taste or taste masking, color, light stability.

The invention is illustrated in more detail by the following non-limiting examples where if not indicated otherwise Methocel E15LV (HMPC) and Surelease (ethylcellulose) have been used.

EXAMPLE 1

Immediate Release Tolterodin Composition

Tolterodine tartrate and microcrystalline cellulose are mixed. Demineralised water is added and mixed. From the homogeneous blend, pellet cores having below composition are made by extrusion and spheronization:

|  | Ingredient | mg |
|---|---|---|
| Pellets | Tolterodine tartarte | 4.0 |
|  | Microcrystalline cellulose | 136.0 |

Thus prepared pellets are filled into capsules and may be administered every 8 or 12 hours.

EXAMPLE 2

Sustained Release Tolterodin Composition

|  | Ingredient | mg |
|---|---|---|
| Pellets | Tolterodine tartarte | 4.0 |
|  | Microcrystalline cellulose | 136.0 |
| Coating | Ethylcellulose | 14.4 |
|  | HPMC | 1.2 |

Tolterodine tartrate and microcrystalline cellulose are mixed. Demineralised water is added and mixed. From the homogeneous blend, pellet cores are made by extrusion and spheronization. Dry pellet cores are coated with the coating dispersion prepared in following steps. First, ethylcellulose polymer dispersions with demineralised water is prepared. Separately, hypromellose (HPMC) is dissolved in water, added to ethylcellulose dispersion and mixed. The resulting dispersion (ratio of Ethylcellulose and HPMC is 12:1) used for coating of the pellet cores in a fluid-bed device, giving a coating which amounts to 10% of the composition weight. Coated pellets are filled into capsules. The Figure shows a dissolution profile of tolterodine formulation prepared according to Example 2.

EXAMPLE 3

Sustained Release Tolterodin Composition

The process of Example 2 is repeated, whereas the amounts of ethylcellulose and HPMC are 22.8 and 1.9 mg per one capsule respectively giving a 15% by weight coating (ratio of polymers 12:1). The formulation dissolves slower than that of Example 2, where 70% of active dissolved in 3 hours, here around 35% dissolves in 3 hours and around 45%, 65%, and 85% in 4, 8, and 16 hours respectively.

EXAMPLE 4

Sustained Release Tolterodin Composition

The process of Example 2 is repeated, whereas the amounts of ethylcellulose and HPMC are 13.1 and 1.7 mg per one capsule respectively giving a 9% by weight coating (ratio of polymers 9:1). The formulation dissolves as follows: 15% in 1 hour, 51% in 2 hours, 73% in 3 hours, 85% in 4 hours and 95% in 7 hours.

EXAMPLE 5

Sustained Release Tolterodin Composition

The process of Example 2 is repeated, whereas the amounts of ethylcellulose and HPMC are 14.4 and 2.4 mg per one capsule respectively giving a 11% by weight coating (ratio of polymers 6:1). The dissolution of this formulation is faster to that of Example 2.

EXAMPLE 6

Sustained Release Tolterodin Composition

The process of Example 2 is repeated, whereas the amounts of ethylcellulose and HPMC are 18.0 and 1 mg per one capsule respectively giving a 12% by weight coating (ratio of polymers 18:1). The dissolution of this formulation is similar to that of Example 3.

EXAMPLE 7

Sustained Release Tolterodin Composition

The process of Example 2 is repeated, whereas the ratio of ethylcellulose and HPMC is 8:1 giving a 9% by weight coating. The formulation dissolves as follows: 67% in 3 hours, 80% in 4 hours and 95% in 8 hours.

EXAMPLE 8

Tolterodin Composition

The process of Example 2 is repeated, with HMPC of viscosity 5 cP and the amounts of ethylcellulose and HPMC 15.6 and 1.2 mg per one capsules (ratio of polymers 1:1). Coated pellets filled into capsules subjected to in vitro dissolution testing show great inter-capsule variability.

EXAMPLE 9

Tolterodin Composition

The process of Example 3 is repeated, with HMPC of viscosity 4000 cP and the amounts of ethylcellulose and HPMC 22.8 and 1.9 mg per one capsules. The dissolution of this formulation is slower than any of the above.

EXAMPLE 10

Sustained Release Tolterodin Composition

The process of Example 2 is repeated, whereas the amounts of ethylcellulose and HPMC are both 7.3 mg per one capsule respectively giving a 10% by weight coating (ratio of polymers 1:1). The dissolution of this formulation is faster than any of the above.

EXAMPLE 11

Sustained Release Tolterodin Composition

|  | Ingredient | mg |
| --- | --- | --- |
| Pellets | Tolterodine tartarte | 4.0 |
|  | Microcrystalline cellulose | 130.0 |
|  | Ethylcellulose | 6.0 |
| Coating | Ethylcellulose | 7.3 |
|  | HPMC | 7.3 |

Tolterodine tartrate, microcrystalline cellulose and part of ethylcellulose are blended with small amount of water into homogeneous blend from which pellet cores are made by extrusion and spheronization. Dry pellet cores are coated with the coating dispersion of Example 8. Within first hour almost 50% dissolves, however between 7 and 16 hours less dissolves as compared to Example 2.

EXAMPLE 12

Sustained Release Tolterodin Composition

|  | Ingredient | mg |
| --- | --- | --- |
| Pellets | Tolterodine tartarte | 4.0 |
|  | Microcrystalline cellulose | 136.0 |
| Coating | Ethylcellulose | 20.0 |
|  | HPMC | 1.9 |
|  | talc | 6.1 |

Dry pellet cores prepared as in Example 2 above are coated with the coating dispersion prepared in three steps. First, ethylcellulose polymer dispersions with demineralised water is prepared. Separately, HPMC is dissolved in water and talc is homogenously dispersed in water. Finally both solution and dispersion are added to ethylcellulose dispersion and mixed. The resulting dispersion is used for coating of the pellet cores in a fluid-bed device giving a 13% by weight coating (calculated on polymers, where ratio of polymers is 10:1)

EXAMPLE 13

Taste Masking Sustained Release Tolterodin Composition

The coated pellets prepared according to Examples 2 are additionally coated with a following taste masking coating:

|  | Ingredient | mg |
| --- | --- | --- |
| Taste masking coating | HPMC (Pharmacoat 606) | 4.8 |
|  | PEG 6000 | 0.5 |
|  | Talc | 0.3 |
|  | Titanium dioxide | 0.4 |
|  | Vanillin | 0.1 |

The coating dispersion is prepared in following steps: (a) HPMC is dispersed in ⅓ of water, preheated to 80° C. and stirred until uniform wet dispersion is obtained. Second third of cold water is added while stirring, dispersion is cooled to temperature below 30° C. and PEG 6000 in added. (b) talc, titanium dioxide and vanilla is dispersed in remaining water using high shear mixer and added to polymer dispersion, which is applied pellets in a fluid-bed device. Pellets are subsequently filled into capsules.

The invention claimed is:

1. A sustained release pharmaceutical composition comprising:
   a) a coating comprising ethylcellulose and hydroxypropylmethyl cellulose (HPMC), with a viscosity in the range of 12 to 18 cP; and
   b) cores, wherein the cores consist of a homogenous blend of predetermined amounts of tolterodine or a salt thereof and microcrystalline cellulose, wherein the amount of tolterodine or a salt thereof is from 0.5 to 10% by weight of a core and wherein the cores are pellets made by extrusion and spheronisation or by direct rotor pelletization so as to be uniform in size and shape, and wherein, in a dissolution test of said sustained release pharmaceutical composition, 15 to 55% of tolterodine will be detected in solution after 2 hours, 30 to 80% in 3 hours, 40 to 90% in 4 hours, 60 to 99% in 8 hours and 85% or more in 16 hours, when subjected to dissolution test according to USP, using Apparatus 1 (rotating basket) at 100 rpm with 900 ml of phosphate buffer (50 mM) at pH 6.8 and 37° C.

2. The sustained release pharmaceutical composition according to claim 1 wherein the salt of tolterodine in the cores is tartrate.

3. The sustained release pharmaceutical composition according to claim 1, wherein in the cores, the amount of tolterodine or salt thereof is 4 mg and the amount of microcrystalline cellulose is 136 mg and the pharmaceutical composition is in the form of a capsule or tablet.

4. A sustained release pharmaceutical composition comprising:
   (i) the cores according to claim 1, and
   (ii) a layer of coating on the cores, wherein the coating comprises ethylcellulose and hydroxypropylmethyl cellulose (HPMC), and wherein the weight ratios of ethylcellulose to HPMC are between 8:1 and 13:1 and the weight of the coating is between 9 and 12% by weight relative to the coated core.

5. The sustained release pharmaceutical composition according to claim 4 wherein the ethylcellulose comprises oleic acid.

6. The sustained release pharmaceutical composition according to claim 4, wherein 50% to 75% of tolterodine will be detected in solution in 3 hours, 70% to 90% in 4 hours, 80% to 99% in 8 hours, when subjected to dissolution test according to USP, using Apparatus 1 (rotating basket) at 100 rpm with 900 ml of phosphate buffer (50 mM) at pH 6.8 and 37° C.

7. The sustained release pharmaceutical composition according to claim 4, further comprising an additional coating on the cores.

8. The sustained release pharmaceutical composition according to claim 7 wherein the additional coating provides for taste masking.

9. A process for the manufacture of a sustained release pharmaceutical composition comprising:
   a. preparing pellets containing only tolterodine and microcrystalline cellulose by extrusion and spheronisation; and
   b. coating said pellets with ethylcellulose and hydroxypropylmethyl cellulose (HPMC), with a viscosity in the range of 12 to 18 cP.

10. A process for the manufacture of a sustained release pharmaceutical composition comprising:
    a. preparing homogenous cores containing only tolterodine and microcrystalline cellulose; and
    b. coating said cores with ethylcellulose and hydroxypropylmethyl cellulose (HPMC), with a viscosity in the range of 12 to 18 cP.

11. A process according to claim 9 or claim 10, wherein the ratio of ethylcellulose to hydroxypropylmethyl cellulose (HPMC) is from 8:1 to 18:1.

* * * * *